(12) United States Patent
Stonecipher

(10) Patent No.: US 11,931,550 B2
(45) Date of Patent: *Mar. 19, 2024

(54) SYRINGE ADAPTER AND GUIDE FOR FILLING AN ON-BODY INJECTOR

(71) Applicant: AMGEN INC., Thousand Oaks, CA (US)

(72) Inventor: Brian Stonecipher, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/840,253

(22) Filed: Jun. 14, 2022

(65) Prior Publication Data

US 2022/0305203 A1    Sep. 29, 2022

Related U.S. Application Data

(63) Continuation of application No. 16/095,018, filed as application No. PCT/US2017/029109 on Apr. 24, 2017, now Pat. No. 11,389,588.

(Continued)

(51) Int. Cl.
   *A61M 5/178*    (2006.01)
   *A61M 5/142*    (2006.01)
   (Continued)

(52) U.S. Cl.
   CPC ...... *A61M 5/1782* (2013.01); *A61M 5/14248* (2013.01); *A61M 39/04* (2013.01);
   (Continued)

(58) Field of Classification Search
   CPC ............ A61M 5/1782; A61M 5/14248; A61M 39/04; A61M 2005/1581;
   (Continued)

(56) References Cited

U.S. PATENT DOCUMENTS 5,779,676 A    7/1998    Kriesel et al.
5,957,891 A *  9/1999    Kriesel ............... A61M 31/002
                                                   604/890.1

(Continued)

FOREIGN PATENT DOCUMENTS

WO    WO-9930769 A1    6/1999
WO    WO-2015177652 A1    11/2015

OTHER PUBLICATIONS

International Search Report for International Application No. PCT/US2017/029109, dated Jul. 18, 2017.

(Continued)

*Primary Examiner* — Theodore J Stigell
(74) *Attorney, Agent, or Firm* — MARSHALL, GERSTEIN & BORUN LLP; Michael P. Furmanek

(57) ABSTRACT

A system and a method for filling an on-body injector includes a needle of the prefilled syringe being aligned with a fill port of the on-body injector. The needle may then be inserted into a guide of a needle cover attached to the on-body injector. An adapter attached to the syringe barrel may guide the needle into a center of the bore of the guide and into the fill port of the on-body injector. The needle may be inserted into the fill port and the adapter may be mechanically coupling to the guide. After the adapter is mechanically coupled to the guide, a volume of the drug of the prefilled syringe may be dispensed into a reservoir of the on-body injector. Once the reservoir is filled to a desired amount, the needle may be removed from the fill port by decoupling the adapter from the guide.

14 Claims, 7 Drawing Sheets

Related U.S. Application Data

(60) Provisional application No. 62/330,354, filed on May 2, 2016.

(51) Int. Cl.
*A61M 39/02* (2006.01)
*A61M 39/04* (2006.01)
*A61M 5/158* (2006.01)

(52) U.S. Cl.
CPC ............ *A61M 2005/1581* (2013.01); *A61M 2039/0205* (2013.01); *A61M 2207/10* (2013.01); *A61M 2209/045* (2013.01)

(58) Field of Classification Search
CPC ...... A61M 2039/0205; A61M 2207/10; A61M 2209/045; A61M 2205/6045; A61M 2039/1077
See application file for complete search history.

(56) References Cited

U.S. PATENT DOCUMENTS

| | | | |
|---|---|---|---|
| 8,372,057 B2* | 2/2013 | Cude | A61M 39/10 604/533 |
| 11,389,588 B2* | 7/2022 | Stonecipher | A61M 39/04 |
| 2006/0200085 A1* | 9/2006 | Watts | A61L 2/07 604/240 |
| 2007/0267092 A1 | 11/2007 | Rink et al. | |
| 2009/0143732 A1 | 6/2009 | O'Connor et al. | |
| 2010/0130932 A1 | 5/2010 | Yodfat et al. | |
| 2010/0243099 A1 | 9/2010 | Yodfat | |
| 2015/0065959 A1 | 3/2015 | Carter et al. | |
| 2015/0157537 A1 | 6/2015 | Lanigan et al. | |
| 2015/0359967 A1* | 12/2015 | Steel | A61M 5/20 604/192 |
| 2016/0008536 A1* | 1/2016 | Gravesen | F16L 29/02 141/2 |

OTHER PUBLICATIONS

Written Opinion of the International Searching Authority for International Application No. PCT/US2017/029109, dated Jul. 18, 2017.

* cited by examiner

SYRINGE ADAPTER AND GUIDE FOR FILLING AN ON-BODY INJECTOR

CROSS-REFERENCE TO RELATED APPLICATIONS

This is a continuation of U.S. patent application Ser. No. 16/095,018, filed Oct. 19, 2018, which is the United States national phase of and claims priority to International Patent Application No. PCT/US17/29109, filed Apr. 24, 2017, which claims priority to U.S. Provisional Patent Application No. 62/330,354, filed May 2, 2016, the entire contents of each of which are hereby expressly incorporated by reference herein.

FIELD OF THE DISCLOSURE

The present disclosure is directed to filling a drug delivery device and, in particular, to a method and system for filling an on-body injector using a syringe adapter and guide.

BACKGROUND

An on-body injector is a disposable drug delivery device and offers a convenient method for self-administering a drug. An on-body injector may adhere to a patient's skin and may be programmed to inject an insertion needle into the patient's skin to deliver a drug when the device is activated. After drug delivery is complete, the needle can retract back into the device housing and the patient may remove and dispose of the device.

FIGS. 1 and 2 illustrate a known system and method for filling an on-body injector 10 with a drug using a prefilled syringe 12. Typically, a healthcare provider may fill an empty device 10 with a protective needle cover 14 attached to an underside surface of the device 10. The needle cover 14 seals the device to keep a fill port 16 and a drug delivery opening 15 sterile while also providing a syringe guide 20 for filling the device 10. The healthcare provider may align a needle 22 of the syringe 12 with the fill port 16 and then insert the needle 22 through a bore 24 of the guide 20 and into the fill port 16 of the device.

FIG. 2 illustrates a cross-sectional view of the guide 20, illustrating the syringe 12 in position for filling a reservoir 18 of the on-body injector 10. A top surface 28 of the guide 20 meets a lower surface 36 of a distal end 30 of the syringe 12 when the syringe 12 is inserted into the bore 24 of the guide 20, thereby preventing the needle 22 from being inserted too far into the reservoir 14. The bore 24 of the guide 20 is curved to help align the needle 22 with the fill port 16. To dispense the drug, the healthcare provider depresses a plunger 26 of the syringe 12.

SUMMARY

In accordance with a first exemplary aspect, a system for filling an on-body injector using a prefilled syringe may include an on-body injector. The on-body injector may include a housing having an interior surface defining an interior cavity and an exterior surface. The on-body injector may further include a reservoir disposed within the interior cavity and configured to receive a volume of a drug. A drug delivery member may be in fluid communication with the reservoir, and configured to extend beyond the exterior surface of the housing through an opening in the housing. A fill port may include an inlet disposed on the exterior surface of the housing and may be in fluid communication with the reservoir. The system may include a needle cover attached to a portion of the exterior surface of the housing and may cover the opening and the fill port. A guide of the needle cover may be coaxially aligned with the fill port and may have an interior surface that defines a bore. The system may include a prefilled syringe having a barrel with a distal end and a barrel reservoir containing a volume of a drug. A needle of the prefilled syringe may be in fluid communication with the barrel reservoir and may be disposed at the distal end of the barrel. An adapter may be attached to the distal end of the barrel and may surround a portion of the needle. The adapter may be configured to mechanically couple to the guide of the needle cover when the adapter is positioned inside the bore of the guide.

In accordance with a second exemplary aspect, a system for filling an on-body injector using a prefilled syringe may include an on-body injector. The on-body injector may include a housing having an interior surface defining an interior cavity and an exterior surface. The on-body injector may further include a reservoir disposed within the interior cavity and configured to receive a volume of a drug. A drug delivery member may be in fluid communication with the reservoir, and configured to extend beyond the exterior surface of the housing through an opening in the housing. A fill port may include an inlet disposed on the exterior surface of the housing and may be in fluid communication with the reservoir. The system may include a needle cover attached to a portion of the exterior surface of the housing and may cover the opening and the fill port. A guide of the needle cover may be coaxially aligned with the fill port and may have an interior surface that defines a tapered bore. The system may include a prefilled syringe having a barrel with a distal end and a barrel reservoir containing a volume of a drug. A needle of the prefilled syringe may be in fluid communication with the barrel reservoir and may be disposed at the distal end of the barrel. An adapter may be attached to the distal end of the barrel and may surround a portion of the needle. The adapter may have a tapered exterior surface that is complementary with the interior surface of the guide.

In accordance with a third exemplary aspect, a method of securing a prefilled syringe to an on-body injector for filling may include inserting a needle of a prefilled syringe into a guide of a needle cover attached to an on-body injector, where the prefilled syringe may include an adapter attached to the syringe and configured to guide the needle of the prefilled syringe to a fill port of the on-body injector. Next, the method may include inserting the needle into the fill port where the fill port may be in fluid communication with a reservoir of the on-body injector. Then, the method may include coupling the adapter to the guide and dispensing a volume of a drug of the prefilled syringe into the reservoir of on-body injector.

In further accordance with any one or more of the foregoing first, second, or third aspects, a system for filling an on-body injector and/or method a method of securing for filling an on-body injector may further include any one or more of the following forms. In one form of the system, a tip of the needle of the prefilled syringe may be positioned within the fill port when the prefilled syringe is inserted into the bore of the guide.

In one form of the system, the interior surface of the guide may be tapered, and the adapter may further include a tapered exterior surface that is substantially complementary with the tapered interior surface of the bore.

In one form of the system, the interior surface of the guide may be straight-walled, and the adapter may further include a straight-walled exterior surface that is substantially complementary with the straight-walled interior surface of the bore.

In one form of the system, the adapter may further include a compressive O-ring disposed on the exterior surface of the adapter.

In one form of the system, the adapter may further include an exterior surface having a detent, and the guide may further include a groove formed in the interior surface of the guide and configured to receive the detent when the adapter is positioned inside the bore of the guide.

In one form of the system, the adapter may further include a male lock fitting and the guide may further include a female lock fitting configured to couple to the male lock fitting when the prefilled syringe is inserted into the bore of the guide.

In one form of the system, the adapter and the guide may be mechanically coupled by friction fit when the adapter is positioned inside the bore of the guide In one form of the system, the guide may further include a shoulder having a surface disposed within the bore and the adapter may further include a nose having a surface that is substantially complementary with the surface of the shoulder and is configured to mate with the surface of the shoulder when the guide and the adapter are mechanically coupled.

In one form of the system, the adapter may further include a female lock fitting and the guide may further include a male lock fitting configured to couple to the female lock fitting when the adapter is inserted into the bore of the guide.

In one form of the system, the guide may further include a detent disposed on the interior surface of the guide, and wherein the adapter may further include an exterior surface having a groove that is configured to receive the detent when the adapter is positioned inside the bore of the guide.

In one form of the system, the adapter and the guide may magnetically couple when the adapter is positioned inside the bore of the guide.

In one form of the method, coupling the adapter to the guide may include coupling a female lock fitting of the guide with a male lock fitting of the adapter.

In one form of the method, dispensing a volume of the drug may be performed after a detent of the adapter couples with a receiving groove of the guide.

In one form of the method, coupling the adapter to the guide may include moving a tapered surface of the adapter into a tapered bore of the guide so that the adapter is coupled to the guide by friction-fit.

In one form of the method, coupling the adapter to the guide may include frictionally engaging a tapered exterior surface of the adapter with a tapered interior surface of the guide.

In one form of the method, coupling the adapter to the guide may include compressing an O-ring disposed about an exterior surface of the adapter against an interior surface of the guide to couple the adapter and the guide by friction fit.

In one form of the method, coupling the adapter to the guide may include pushing a protruded ring disposed on an exterior surface of the adapter into a groove formed in an interior surface of the guide where the groove may be shaped to receive the protruded ring and secure the adapter to the guide.

In one form, the method may include removing the needle from the fill port by decoupling the adapter from the guide.

DETAILED DESCRIPTION

Figure 3:
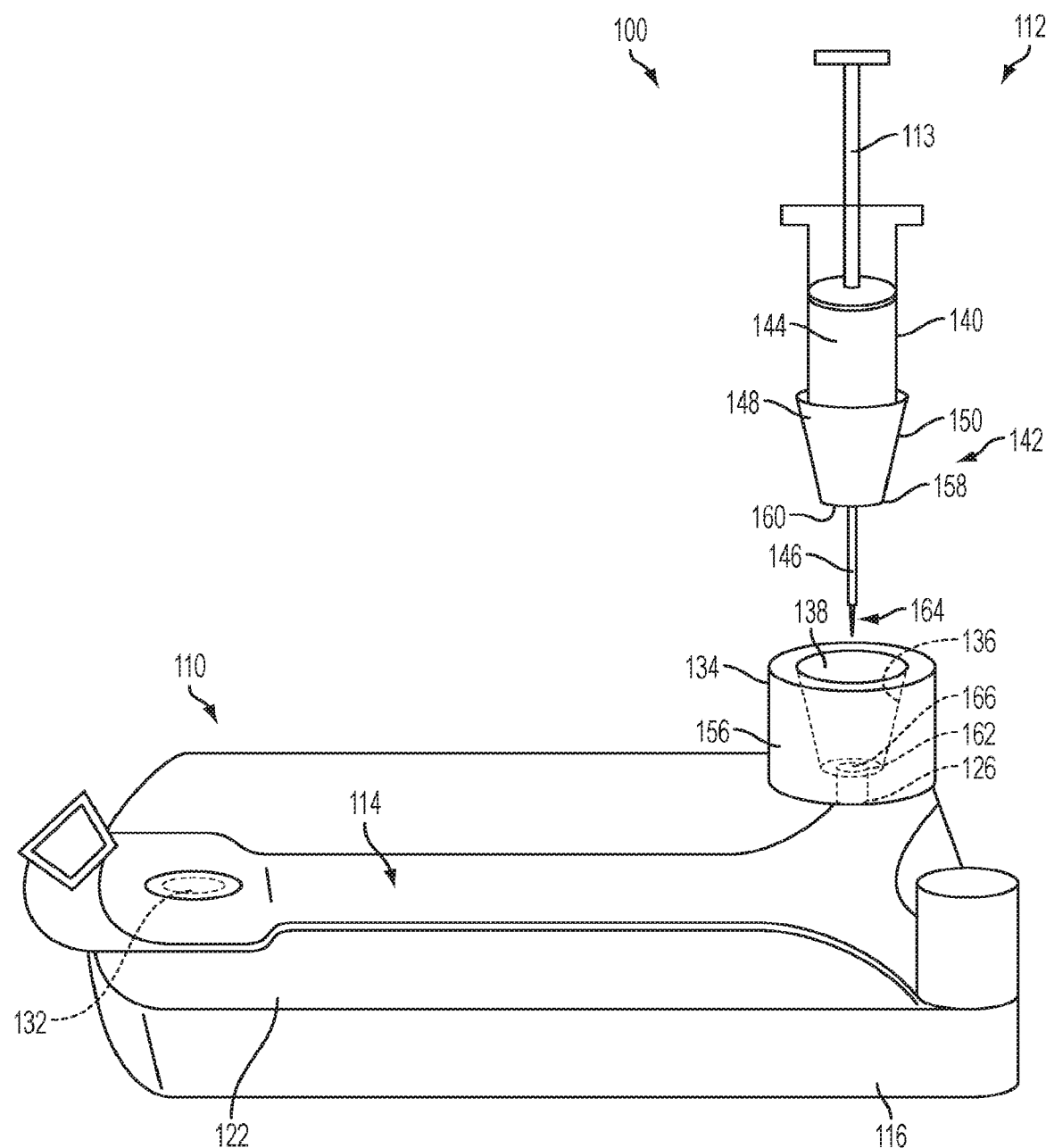
FIG. 3 illustrates an exploded perspective view of a system for filling an on-body injector using a prefilled syringe in accordance with the teachings of an exemplary arrangement of the present disclosure.
Figure 4:
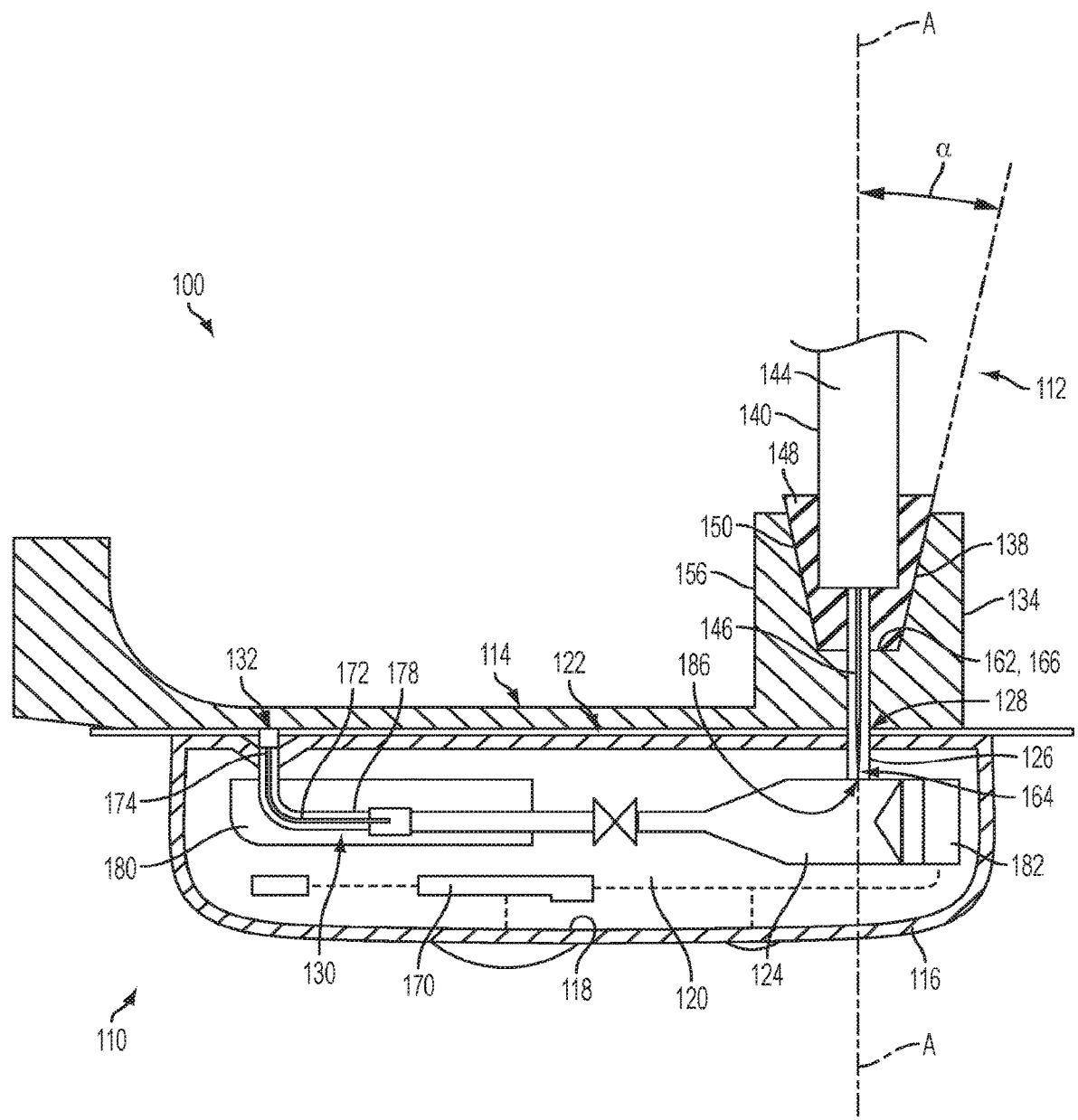
FIG. 4 illustrates a cross-sectional view of the system of FIG. 3 in a coupled position for filling the on-body injector.

Turning now to specific examples of the disclosure, FIGS. 3-4 illustrate an improved system and method for securing a prefilled syringe to an on-body injector for filling.

Referring now to FIGS. 3-4, a filling system 100, or filling kit, includes an empty on-body injector 110, a prefilled syringe 112 containing a drug, and a needle cover 114 attached to the on-body injector 110. The on-body injector 110, which may also be referred to herein as the device, includes a housing 116 with an interior surface 118 that defines an interior cavity 120, and an exterior surface 122. A reservoir 124 is disposed within the interior cavity 120 and is configured to receive a volume of the drug through a fill port 126. The fill port 126 is in fluid communication with the reservoir 124 and has an inlet 128 disposed on the exterior surface 122 of the housing 116. A drug delivery member 130 is also disposed within the housing 116 and is in fluid communication with the reservoir 124. The drug delivery member 130 is configured to extend beyond the exterior surface 122 of the housing 116 through an opening 132 to deliver a drug to a patient, as described further below.

The needle cover 114 is attached to a portion of the exterior surface 122 of the housing 116 and can cover the opening 132 and the fill port 126. The needle cover 114 includes a syringe guide 134 coaxially aligned with an axis A-A of the fill port 126 to guide and secure the prefilled syringe 112 to the on-body injector 110 when filling the device 110. The guide 134 includes an interior surface 136 that defines a bore 138.

The prefilled syringe 112 includes a barrel 140 having a distal end 142, a barrel reservoir 144 containing a volume of the drug, and a needle 146 attached to the barrel 140 at the distal end 142 of the syringe 112. The needle 146 is in fluid communication with the barrel reservoir 144. A syringe adapter 148 is configured to mechanically couple to the guide 134 when the adapter 148 is positioned inside the bore 138 of the guide 134. In the depicted version, the adapter 148 is attached to the distal end 142 of the barrel 140 and surrounds a portion of the needle 146, leaving a portion of the needle 146 exposed. The adapter 148 may be attached, or otherwise fixed or coupled, to the syringe barrel 140 by a snap-fitting, friction-fitting, and/or by threading. In other versions, the adapter 148 can be formed integrally with the syringe 112, such as with the syringe barrel 144, for example. The syringe adapter 148 may be attached to the barrel 140 before or after the syringe 112 is filled with the drug. The system 100 can be provided as a kit to a healthcare provider or patient and includes the prefilled syringe 112 with the attached syringe adapter 148 and an empty on-body injector 110 with the attached needle cover 114.

In one method for filling the on-body injector 110, a user aligns the needle 146 of the prefilled syringe 112 with the axis A-A of the fill port 126 and then inserts the needle into the guide 134 of the needle cover 114. The adapter 148 attached to the syringe barrel 140 guides the needle 146 into a center of the bore 138 of the guide 134 and into the fill port 126 of the on-body injector 110. The user then inserts the needle 146 into the fill port 126 and the adapter 148 becomes mechanically coupled to the guide 134. After the adapter 148 is mechanically coupled to the guide 134, the user depresses a plunger 113 on the syringe 112 to dispense the drug into the reservoir 124 of the on-body injector 110. Once the reservoir 124 is filled to a desired amount, the needle 146 may be removed from the fill port 126 by decoupling the adapter 148 from the guide 134.

The adapter 148 and the guide 134 mechanically couple so that the syringe 112 is secured to the device 110 before filling the on-body injector 110 with the drug. In the example of FIGS. 3-4, the guide 134 and the adapter 148 may mechanically couple by interference fit. The adapter 148 has an exterior surface 150 that is substantially complementary with the interior surface 136 of the guide 134. In this case, the exterior surface 150 of the adapter 148 and the interior surface 136 of the guide 134 are tapered. The adapter 148 has a truncated conical shape and the bore 138 is shaped to receive the conical shape of the adapter 148. To couple the adapter 148 to the guide 134, the adapter 148 is inserted into the bore 138 of the guide 134 until the tapered surface 150 of the adapter 148 and the tapered surface 136 of the guide 134 meet and couple by friction. As used herein, the term "substantially complementary" refers to a summation of two angles that approaches 90°, the summation typically being within ±10°, within ±5°, and/or within ±2° of 90°. As used herein, two surfaces that are substantially complementary, substantially supplementary, or similarly shaped may be referred to as "corresponding surfaces." In some versions, the exterior surface 150 of the adapter 148 and the interior surface 136 of the guide 134 can be disposed at an angle α (shown in FIG. 4) relative to the axis A-A. In some versions, the angle α can be in a range of approximately 1° to approximately 60°, or in a range of approximately 1° to approximately 45°, or in a range of approximately 1° to approximately 30°, or in a range of approximately 1° to approximately 15°, or in a range of approximately 1° to approximately 5°, or in a range of approximately 5° to approximately 60°, or in a range of approximately 5° to approximately 45°, or in a range of approximately 5° to approximately 30°, or in a range of approximately 5° to approximately 15°, or in a range of approximately 5° to approximately 10°, or in a range of approximately 15° to approximately 60°, or in a range of approximately 15° to approximately 45°, or in a range of approximately 15° to approximately 30°, or in a range of approximately 15° to approximately 20°, or any other angle larger or smaller than the angles stated above depending on the specific application and desired outcome. In one version, the angle α can be approximately 0°, within appropriate tolerances based on the type of manufacturing utilized to manufacturer, form and/or finish the exterior surface 150 of the adapter 148 and the interior surface 136 of the guide 134. In such a version, the surfaces 150, 136 can be described as being straight-walled. In fact, based on the type of manufacturing method used, when the angle α of the interior surface 136 of the guide 134 is disposed at an angle α of approximately 0°, such an interior surface 136 can be described as "tapered" because a molding process, for example, may necessarily require some degree of tapering in the molding draft. As such, the term "tapered" as used herein is intended to also cover those situations where the surface 150, 136 are disposed at approximately 0° relative to the axis A-A. Additionally, in versions where the angle α is approximately 0°, the interior surface 150 of the adapter 148 and the exterior surface 136 of the guide 134 can be approximately parallel to each other and approximately parallel to the axis A-A. Finally, while the foregoing has described the exterior surface 150 of the adapter 148 and the interior surface 136 of the guide 134 as sharing the same angle α, in other versions, these two surfaces 150, 136 can have different angles. For example, in one version, the interior surface 136 of the guide 134 can be disposed at an angle α1 that is larger than an angle α2, at which the exterior surface 150 of the adapter 148 is disposed. In another version, the interior surface 136 of the guide 134 can be disposed at an angle α1 that is smaller than an angle α2, at which the exterior surface 150 of the adapter 148 is disposed. In either of these situations, α1 and α2 can fall inside or outside any of the ranges specific above for angle α.

As shown in the illustrated example of FIGS. 3-4, the guide 134 includes a wall 156 that extends outwardly from a portion of the exterior surface 122 of the housing 116 (underside of the device 110). When the adapter 148 and the guide 134 are mechanically coupled, a portion of the adapter 148 may contact or rest on a portion of the guide wall 156, suspending the needle 146 within the fill port 126 and limiting axial displacement of the needle 146 into the on-body injector 110. As shown best in FIG. 3, the adapter 148 has a nose 158 at the distal end 142 of the syringe 112. The nose 158 may have a surface 160 that corresponds to a surface 166 of an interior shelf or shoulder 162 of the guide 134. As the surfaces make contact, the surface 160 of the nose 158 couples to the surface 166 of the shoulder 162, the shoulder 162 stopping the needle 146 from moving further into the fill port 126. The height of the guide wall 156 and placement of the adapter 148 on the syringe 112, and therefore the length of the exposed needle 146, are configured so that a tip 164 of the needle 146 reaches a predetermined position within the on-body injector 110 for optimal delivery of the drug into the reservoir 124. The guide 134 and corresponding adapter 148 reduce the risk of inserting the needle 146 too far into the on-body injector 110 and puncturing a wall of the reservoir 124 and/or blocking the tip 164 of the needle 146 from delivering the drug. The system is not limited to the syringe adapter 148 and guide 134 illustrated in FIGS. 3-4, and may include a syringe adapter and guide pair having a configuration that adequately positions the needle 146 in the on-body injector 110 for delivery.

The system 100 illustrated and described herein advantageously facilitates the process of filling an on-body injector 100 with a prefilled syringe 112. The tapered shape of the adapter 148 and tapered shape of the bore 138 of the guide 134 helps align the needle 146 with the axis A-A of the fill port 126 and guides the syringe 112 into position. The corresponding surfaces (e.g. exterior surface 150 of the adapter 148 and interior surface 135 of the guide 134) provide a buffer between the delicate needle 146 and the hard surface of the guide 134. The syringe adapter 148 and guide 134 facilitate accurate and suitable positioning of the needle 146 for filling. Further, the mechanical coupling between the adapter 148 and the guide 134 stabilizes the syringe 112 relative to the on-body injector 110 during filling such that a healthcare provider or user does not have to hold the on-body injector 110 in alignment with the syringe 112 when dispensing the drug into the reservoir 124. In other words, once the adapter 148 is coupled to the guide 134, the needle 146 is secured in place for filling and remains aligned with axis A-A of the fill port 126, at the appropriate depth dictated by contact between surfaces 160 and 166.

The syringe adapter and guide configuration is not limited to the example shown in FIGS. 3-4. The adapter and guide may mechanically couple by other coupling or locking methods such that when the adapter and the guide are coupled, the syringe needle 146 remains aligned with the fill port 126 until the adapter 148 and guide 134 are pulled apart or otherwise decoupled. An audible clicking noise may be incorporated into the coupling mechanism to alert a user that the adapter 146 is coupled to the guide 134 and ready for filling.

In FIGS. 5-10, various alternative configurations of syringe adapters and guides are illustrated in both an uncoupled position and a coupled position. While the present disclosure describes and discusses various adapters and guides having different features, it is contemplated that the different features can be combined in any manner or fashion to achieve desired results. For example, the present disclosure contemplated that the adapter and guide in FIGS. 3-4 can be modified to include any or all of the features of any of FIGS. 5-10 and/or elsewhere discussed herein. The present disclosure contemplated that the adapter and guide in FIGS. 5-6 can be modified to include any or all of the features of any of FIGS. 3-4 and 7-10 and/or elsewhere discussed herein. The present disclosure contemplated that the adapter and guide in FIGS. 7-8 can be modified to include any or all of the features of any of FIGS. 3-6 and 9-10 and/or elsewhere discussed herein. The present disclosure contemplated that the adapter and guide in FIGS. 9-10 can be modified to include any or all of the features of any of FIGS. 3-8 and/or elsewhere discussed herein. Thus, while the following features can be considered as independent alternatives, they can also be complementary features, in that any given adapter and guide pair within the scope of the present disclosure can include any combination of features taken from FIGS. 3-10 and/or elsewhere discussed herein.

Figure 5:
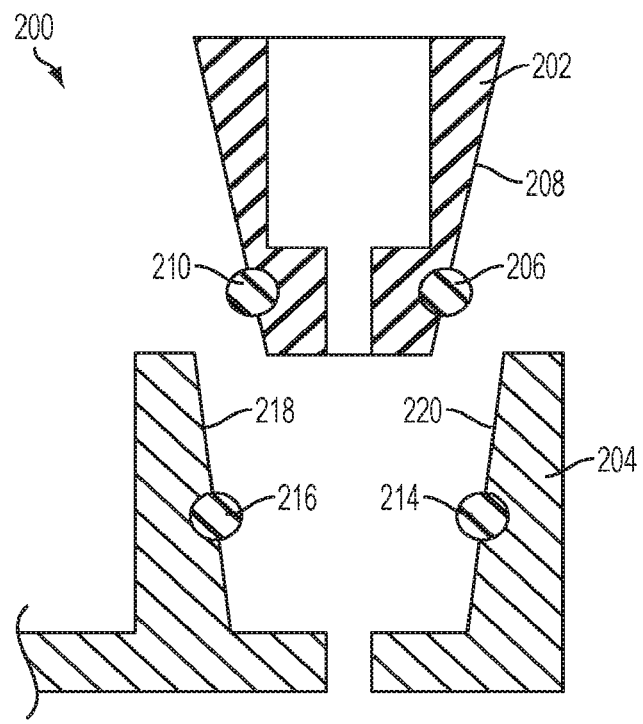
FIG. 5 illustrates a partial exploded cross-sectional view of an exemplary syringe adapter and guide in accordance with the teachings of the present disclosure.
Figure 6:
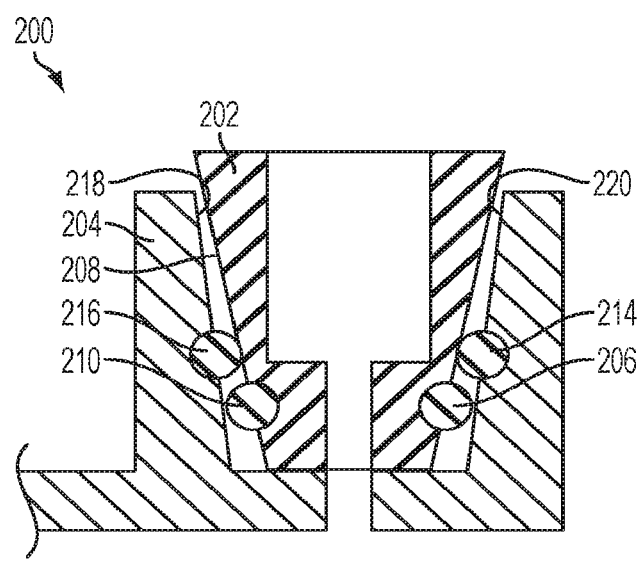
FIG. 6 illustrates a partial cross-sectional view of the syringe adapter and guide of FIG. 5 in a coupled position.

In FIGS. 5-6, a syringe adapter and guide pair 200 includes an adapter 202 having a compressive O-ring 206 disposed within a groove 210 formed in a conical exterior surface 208 of the adapter 202. A guide 204 also includes a compressive O-ring 214 disposed within a groove 216 formed in a complementary conical interior surface 218 of the guide 204. As the adapter 202 is inserted within a bore 220 of the guide 204, the O-ring 206 of the adapter 202 may compress against the interior surface 218 and the O-ring 214 of the guide 204. The adapter 202 and guide 204 mechanically couple when the O-ring 206 of the adapter 202 passes the O-ring 214 of the guide 204 as shown in FIG. 6. The adapter 202 is coupled to the guide 204 by friction fit. In FIG. 6, the O-rings 206, 214 are illustrated as out of contact when the adapter 202 is coupled to the guide 204, but in other versions, the O-rings 206, 214 can be in contact when the adapter 202 and guide 204 are coupled. To decouple the adapter 202 and the guide 204, the adapter 202 may be pulled away from the guide 206, thereby compressing the O-rings 206, 214 to allow the adapter 202 is slide out of the bore 220. While two O-rings 206, 214 are illustrated in FIGS. 5-6, one O-ring disposed on either the interior surface 218 of the guide 204 or the exterior surface 208 of the adapter 202 may sufficiently couple the syringe adapter and guide pair 200 by friction fit.

Figure 7:
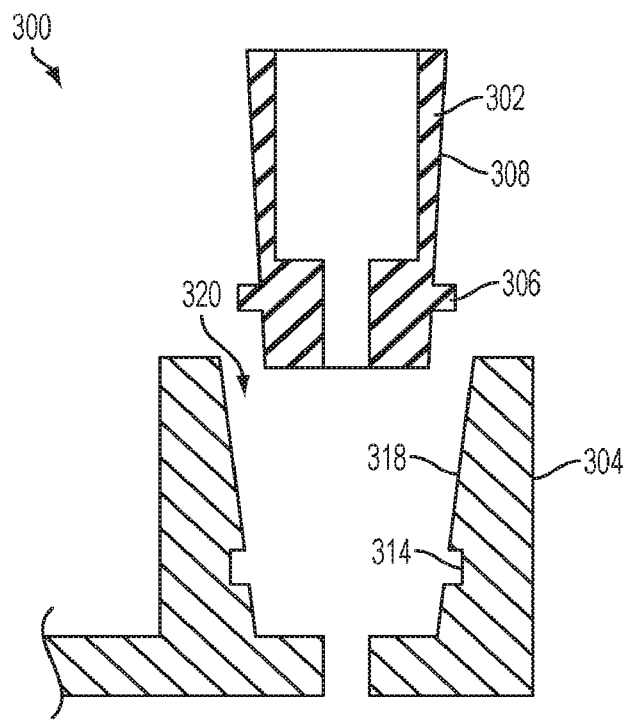
FIG. 7 illustrates a partial exploded cross-sectional view of another exemplary syringe adapter and guide in accordance with the teachings of the present disclosure.
Figure 8:
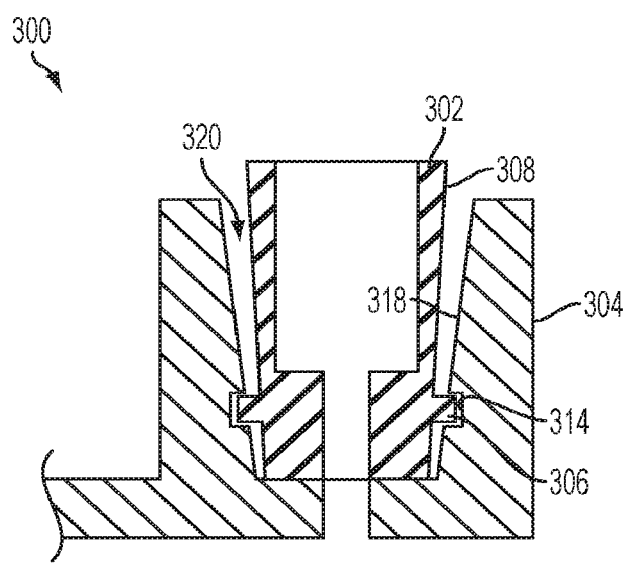
FIG. 8 illustrates a partial cross-sectional view of the syringe adapter and guide of FIG. 7 in a coupled position.

In another exemplary configuration, a syringe adapter and guide pair 300 in FIGS. 7-8 includes an adapter 302 with a detent 306 protruding from a conical exterior surface 308 of the adapter 302. A guide 304 may have a receiving groove 314 formed in a complementary conical interior surface 318 to receive the detent 306. To couple the adapter 302 and the guide 304, the adapter 302 is pushed into a bore 320 of the guide 304 until the detent 306 snaps into the receiving groove 314 formed in the interior surface 318 of the guide 304. Alternatively, the interior surface 318 of the guide 304 may have a detent (not illustrated) and the exterior surface 308 of the adapter 302 may include a groove (not illustrated) configured to receive the detent when the adapter 302 is inserted into the guide 304. The detent may be a hooking mechanism or it may be an annular ring or ridge that is configured to mate with a receiving groove. For the sake of clarity only, FIG. 8 illustrates a certain spacing or gap between the adapter 302 and guide 304 when the two are coupled. In some versions, the adapter 302 and guide 304 maintain a close snug fit, without spacing, when coupled together. Moreover, as suggested above, in some versions, the exterior surface 308 of the adapter 302 and the interior surface 318 of the guide 304 can form a friction tight interference fit when the adapter 302 and guide 304 are coupled. This interference friction fit can assist the detent 306 with the coupling of these components together.

Figure 9:
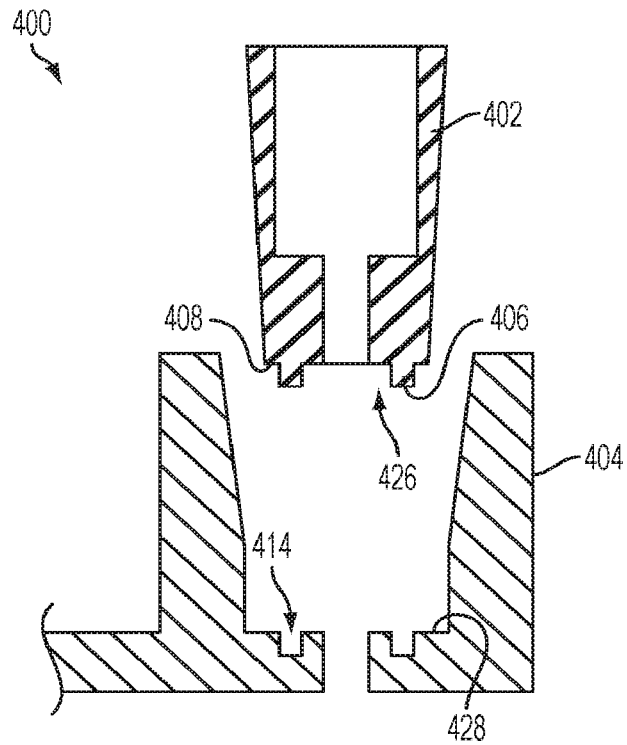
FIG. 9 illustrates a partial exploded cross-sectional view of yet another exemplary syringe adapter and guide in accordance with the teachings of the present disclosure.
Figure 10:
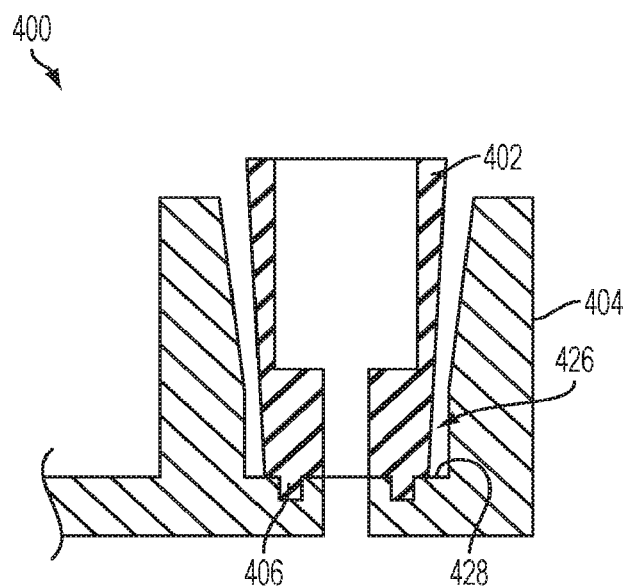
FIG. 10 illustrates a partial cross-sectional view of the syringe adapter and guide of FIG. 9 in a coupled position.

In yet another example, a syringe adapter and guide pair 400 illustrated in FIGS. 9-10 includes a protruded ring 406 that may extend from a surface 408 of a nose 426 of an adapter 402. A groove 414 is formed in a shoulder 428 of a guide 404 and is configured to receive the protruded ring 406. To couple, the adapter 402 is pushed into the guide 404 until the protruded ring 406 snaps into the groove 414. In other configurations, the syringe adapter and guide may mechanically couple by mating a male lock fitting with a corresponding female lock fitting. For example, the coupling mechanism of an adapter and guide may be a conventional bayonet connector. The adapter may include a male fitting having one or more radial pins and the guide may include a female receptor with corresponding L-shaped slots to receive the radial pins. When the adapter is inserted into a bore of the guide, the adapter (i.e. the syringe) may be slightly rotated so that the one or more radial pins may be inserted into the L-shaped slots and locked into place. Again, for the sake of clarity only, FIG. 10 illustrates a certain spacing or gap between the adapter 402 and guide 404 when the two are coupled. In some versions, the adapter 402 and guide 404 maintain a close snug fit, without spacing, when coupled together. Moreover, as suggested above, in some versions, the adapter 402 and the guide 404 can form a friction tight interference fit when the adapter 402 and guide 404 are coupled. This interference friction fit can assist with coupling these components together.

The syringe adapter and guide of any of the foregoing versions may be manufactured using certain materials. For example, certain materials may be used that enhance the mechanical engagement between the corresponding surfaces so that the adapter and guide couple when the adapter is pushed into the guide. In some versions, either or both of the syringe adapter and guide may be a rubber material, a plastic material, a resilient elastomer material, a cork material, or any other suitable material or combination of materials including those having resilient and non-resilient properties. In some versions, one or more of the adapter and guide may include a material that magnetically couples to a material of the other. For example, in one version, one of the guide and the adapter can include a magnetic insert embedded within a plastic material and the other of the guide and adapter can have a magnet such that when the adapter is inserted into the guide, they become magnetically coupled.

As one example, it should be appreciated that in some versions such as that described in reference to FIGS. 3-4, the guide 134 could be made of a hard plastic material and the adapter 146 could be made of or coated with a resilient material such that when the adapter 146 is inserted into the guide 134, the resilient material compresses to exert an outward radial force against the guide 134 to further retain the adapter 146 in the guide 134. Other variations are possible.

Figure 11:
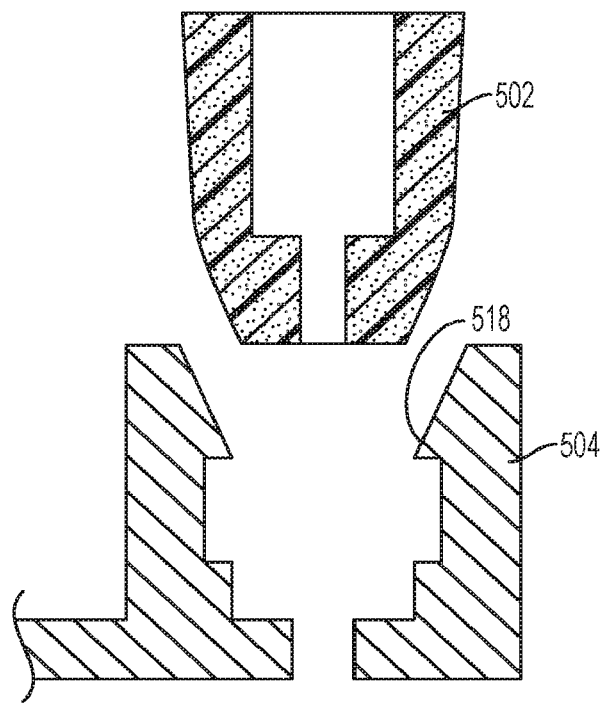
FIG. 11 illustrates a partial exploded cross-sectional view of still another exemplary syringe adapter and guide in accordance with the teachings of the present disclosure.
Figure 12:
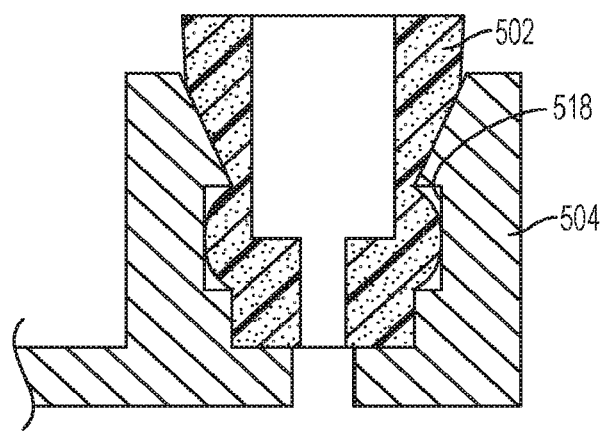
FIG. 12 illustrates a partial cross-sectional view of the syringe adapter and guide of FIG. 11 in a coupled position.

As illustrated in FIGS. 11-12, an adapter 502 may be a moldable material, such as a foam, that compresses when inserted into a guide 504. The moldable material partially expands to fill an interior space defined by an interior surface 518 of the guide 504, thereby keeping the adapter in place. In other examples, the exterior surface of the adapter and the interior surface of the guide may be treated with a coating and/or other additive to enhance the frictional forces between the surfaces. The syringe adapter and guide may be a single material or a combination of materials. For example, the adapter may include a magnetic strip or coating to position and secure the adapter in place relative to the guide.

The exemplary adapter and guide configurations as described and illustrated in FIGS. 3-13 are not limited to the use of the specific on-body injector 110 illustrated in FIG. 4, and may be used with a suitable empty drug delivery device. Referring back to FIG. 4, the exemplary on-body injector 110 will be described in more detail.

The device 110 adheres to the skin of a patient, most likely, but not exclusively, after being placed there by healthcare personnel associated with the procedure. The device 110 automatically injects a drug delivery device 130 from an interior cavity 120 (sealed by the needle cover 114) defined by the housing 116 into the patient to define an injection site. The device 110 automatically actuates a drug supply to deliver a volume of a drug to the patient through an injection site as a single bolus according to the configuration of a controller 170.

The drug delivery device 130 includes a needle 172 with a pointed end 174. The needle 172 has a retracted state wherein the pointed end 174 of the needle is withdrawn inside the cavity 120 defined by the housing 116, as shown in FIG. 4. The needle 172 also has a deployed state wherein the pointed end 174 of the needle 172 projects from the cavity 120 beyond the exterior surface 122 of the housing 116 into the injection site of the patient. The needle 172 may be used in conjunction with a catheter 178, the needle 172 being used to insert the catheter 178 into the patient through the injection site, and the drug passing through the catheter 178 into the patient during administration. The device 110 includes an injector 180 that moves the needle 172 between the retracted and deployed states.

The controller 170 is coupled to the injector 180 and the drug supply. The controller 170 is programmed to control the injector 180 and the drug supply, and may operate the injector 180 to move the needle 172 and the drug supply to deliver the volume of the drug. The controller 170 is disposed within the sealed cavity 120 defined within the disposable housing 116 and programmed prior to being disposed within the sealed cavity 120. Thus, once the controller 170 is disposed in the cavity 120 and the housing 116 is sealed, the controller 170 may not be reprogrammed.

The housing 116 may have an aperture or opening 132 formed therein to permit the needle 172 (and catheter 178) to pass therethrough. According to certain embodiments, the aperture 132 may be unobstructed such that there is no impediment or obstacle to the movement of the needle 172 (and catheter 178) through the opening 132. However, to better maintain the sterility of the needle 172 and the container closure integrity (CCI) of the device 110, a septum may be disposed in or over the aperture 132, or within the cavity 120 defined by the housing 116 so as to overlie the opening 132. In one variant, the septum may be made of rubber. The septum is disposed between the needle and the needle cover 114 in the retracted state. In the deployed state, at least a portion of the needle 172 will emerge from the cavity 120 through the septum. As such, the septum is always present as a barrier between the interior cavity 120 and the external environment.

According to the illustrated embodiment, the drug supply may include a pump 182 and a reservoir 124. According to an embodiment of the present disclosure, the reservoir 124 and pump 182 may be defined in part by a combination of a rigid-walled cylinder and plunger 184 fitted to move along a longitudinal axis of the cylinder. The reservoir 124 may be a flexible pouch. Further, the fill port 126 is in fluid communication with the reservoir 124 and has an inlet 128 disposed on the exterior surface 122 of the housing 116. The fill port 126 may also include a cover disposed in the inlet 128 to close the fill port 126. An outlet 186 of the fill port 126 is fluidly connected to the reservoir 124. One or more filters may be disposed between the inlet 128 and the outlet 186 to limit the passage of air or particulate matter into the reservoir 124 along with the drug.

The above description describes various systems and methods for filling a drug delivery device. It should be clear that the system, drug delivery device, syringe, or methods can further comprise use of a medicament listed below with the caveat that the following list should neither be considered to be all inclusive nor limiting.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Figure 1:
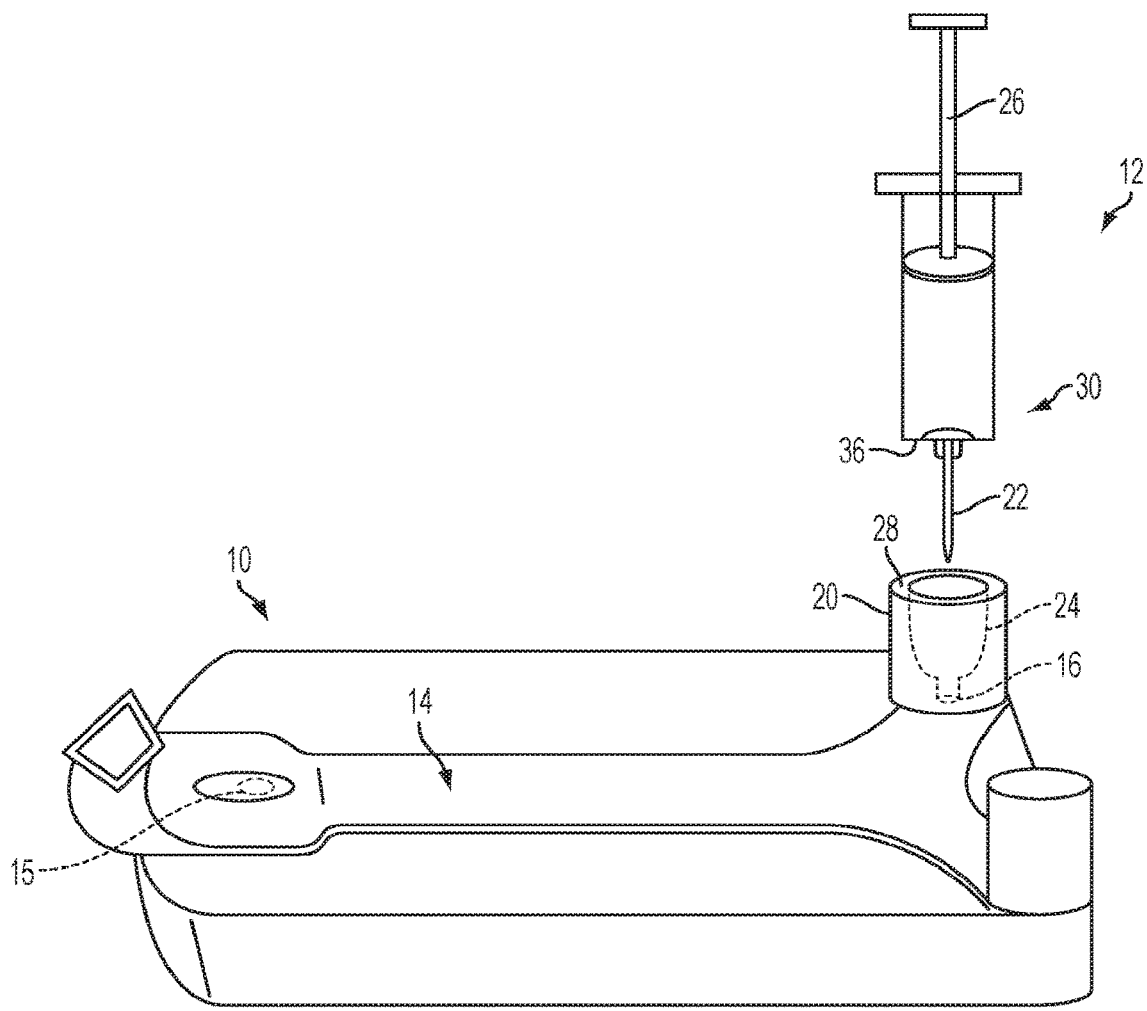
FIG. 1 illustrates a perspective view of a known on-body injector and attached needle cover with an associated prefilled syringe that may be used to fill the on-body injector with a drug.
Figure 2:
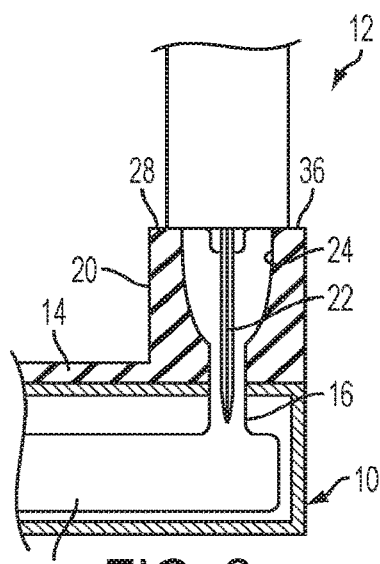
FIG. 2 illustrates a partial cross-sectional view of the needle cover, while the syringe is in position for filling the on-body injector of FIG. 1.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146 B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5ß1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the on-body injector, syringe adapter, needle cover guide, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent application. The appended claims should be construed broadly to include other variants and embodiments of same, which may be made by those skilled in the art without departing from the scope and range of equivalents of the device, needle cover guide, prefilled syringe adapter, systems, methods, and their elements.

What is claimed:

1. An on-body injector system comprising:
an on-body injector comprising:
a housing having an interior surface defining an interior cavity and an exterior surface,
a reservoir disposed within the interior cavity and configured to receive a volume of a drug, and
a fill port having an inlet disposed on the exterior surface of the housing, the fill port being in fluid communication with the reservoir;
a needle cover attached to a portion of the exterior surface of the housing and covering the fill port, the needle cover comprising a guide aligned with the fill port, the guide having an interior surface defining a bore; and
an adapter configured to be received within the guide of the needle cover, the adapter configured to stabilize a prefilled syringe for filling the reservoir,
wherein the adapter has a frustoconical portion that is configured to be received in a tapered interior surface of the guide.

2. The system of claim 1, wherein the adapter is configured to be mechanically coupled to the bore of the guide of the needle cover.

3. The system of claim 1, wherein the adapter is mechanically coupled to the bore of the guide of the needle cover.

4. The system of claim 1, wherein the frustoconical portion of the adapter is substantially complementary with the tapered interior surface of the guide.

5. The system of claim 1, wherein the adapter further comprises a compressive O-ring disposed on the exterior surface of the adapter.

6. The system of claim 1, wherein the adapter further comprises an exterior surface having a detent, and wherein the guide further comprises a groove formed in the interior surface of the guide and configured to receive the detent when the adapter is positioned inside the bore of the guide.

7. The system of claim 1, wherein the adapter further comprises a male lock fitting and the guide comprises a female lock fitting configured to couple to the male lock fitting when the adapter is inserted into the bore of the guide.

8. The system of claim 1, wherein the adapter and the guide are mechanically coupled by friction fit when the adapter is positioned inside the bore of the guide.

9. The system of claim 1, wherein the guide further comprises a shoulder having a surface disposed inside the bore and the adapter further includes a nose having a surface that is substantially complementary with the surface of the shoulder and is configured to mate with the surface of the shoulder when the guide and the adapter are mechanically coupled.

10. The system of claim 1, wherein the adapter further comprises a female lock fitting and the guide comprises a male lock fitting configured to couple to the female lock fitting when the adapter is inserted into the bore of the guide.

11. The system of claim 1, wherein the guide further comprises a detent disposed on the interior surface of the guide, and wherein the adapter further comprises an exterior surface having a groove that is configured to receive the detent when the adapter is positioned inside the bore of the guide.

12. The system of claim 1, wherein the adapter and the guide are magnetically coupled when the adapter is positioned inside the bore of the guide.

13. The system of claim 1, further comprising:
a prefilled syringe comprising:
a barrel having a distal end and a barrel reservoir containing a volume of a drug, and
a needle in fluid communication with the barrel reservoir and disposed at the distal end of the barrel, wherein the distal end of the barrel is configured to be coupled to the adapter for stabilizing the prefilled syringe when the adapter is positioned inside of the bore of the guide.

14. The system of claim 13, wherein a tip of the needle of the prefilled syringe is positioned within the fill port when the distal end of the barrel is coupled to the adapter and the adapter is positioned inside of the bore of the guide.

\* \* \* \* \*